US012616545B2

(12) United States Patent (10) Patent No.: US 12,616,545 B2
Shang (45) Date of Patent: May 5, 2026

(54) ARTICULATED MEMBER

(71) Applicant: Precision Robotics Limited, London (GB)

(72) Inventor: Jianzhong Shang, Dartford (GB)

(73) Assignee: Precision Robotics Limited, London (GB)

( * ) Notice: Subject to any disclaimer, the term of this patent is extended or adjusted under 35 U.S.C. 154(b) by 162 days.

(21) Appl. No.: 18/291,699

(22) PCT Filed: Dec. 9, 2022

(86) PCT No.: PCT/GB2022/053150
§ 371 (c)(1),
(2) Date: Jan. 24, 2024

(87) PCT Pub. No.: WO2023/118788
PCT Pub. Date: Jun. 29, 2023

(65) Prior Publication Data
US 2024/0277437 A1 Aug. 22, 2024

(30) Foreign Application Priority Data
Dec. 21, 2021 (GB) ...................................... 2118678

(51) Int. Cl.
*A61B 34/00* (2016.01)
*A61B 34/30* (2016.01)
*A61M 25/01* (2006.01)
(52) U.S. Cl.
CPC ........ *A61B 34/71* (2016.02); *A61B 2034/301* (2016.02); *A61B 2034/306* (2016.02); *A61M 25/0138* (2013.01); *A61M 25/0147* (2013.01)
(58) Field of Classification Search
CPC ........ A61B 2034/301; A61B 2034/306; A61B 34/30; A61B 34/71; A61M 25/0138; A61M 25/0147
See application file for complete search history.

(56) References Cited

U.S. PATENT DOCUMENTS

| 6,817,974 B2 | 11/2004 | Cooper et al. |
| 2006/0199999 A1* | 9/2006 | Ikeda ..................... A61B 34/71 |
| | | 600/141 |

(Continued)

FOREIGN PATENT DOCUMENTS

| CN | 110269682 A | 9/2019 |
| CN | 106737629 B | 11/2019 |

(Continued)

OTHER PUBLICATIONS

International Search Report and Written Opinion from PCT International Application No. PCT/GB2022/053150 dated Feb. 28, 2023.

(Continued)

*Primary Examiner* — Mohamed G Gabr
(74) *Attorney, Agent, or Firm* — Budzyn IP Law, LLC

(57) ABSTRACT

An articulated member for a surgical instrument, the articulated member including: first proximal and distal joints, each rotatable about a respective axis that extends across a first rotation plane extending longitudinally through the articulated member; second proximal and distal joints, each rotatable about a respective axis that extends across a second rotation plane extending longitudinally through the articulated member perpendicularly to the first rotation plane so that the second proximal and distal joints are rotatable orthogonally relative to the first proximal and distal joints; and a plurality of coupling tendons extending through the articulated member via respective coupling tendon receiving portions. Each coupling tendon extends along the articulated member substantially spaced apart from both the first and second rotation planes so that rotation of one of the proximal and distal joints causes rotation of the other of the respective proximal and distal joints.

14 Claims, 6 Drawing Sheets

(56) References Cited

U.S. PATENT DOCUMENTS

| | | | | |
|---|---|---|---|---|
| 2008/0065098 | A1 | 3/2008 | Larkin | |
| 2010/0160929 | A1 | 6/2010 | Rogers et al. | |
| 2018/0296285 | A1* | 10/2018 | Simi | A61B 10/04 |
| 2020/0038121 | A1* | 2/2020 | Yang | A61B 34/20 |
| 2021/0121259 | A1* | 4/2021 | Simi | A61B 34/37 |

FOREIGN PATENT DOCUMENTS

| | | | |
|---|---|---|---|
| GB | 2550575 | A | 11/2017 |
| JP | 6388628 | B2 | 9/2018 |

OTHER PUBLICATIONS

Search and Examination Report from Great Britain Application No. GB2118678.8 dated May 26, 2022.

* cited by examiner

ARTICULATED MEMBER

CROSS-REFERENCE TO RELATED APPLICATIONS

This Application is a National Stage Application under 35 U.S.C. § 371 of PCT Application No. PCT/GB2022/053150, filed Dec. 9, 2022 which claims priority to UK Patent Application No. GB2118678.8, filed Dec. 12, 2021, the entire contents of which are incorporated by reference herein.

BACKGROUND OF THE INVENTION

1. Field of the Invention

This invention relates to an articulated member for a surgical instrument. The invention has particular application in the field of surgical robotics to facilitate the movement of a surgical instrument end effector for minimally invasive surgical procedures, although the invention is not limited to such application and may also have use in other medical/surgical devices comprising a member that requires articulation through rotation of a plurality of joints.

2. Description of the Related Art

Known surgical instruments forming part of robotic surgical systems comprise a shaft, an articulated portion and an end effector. The shaft may extend from other components of the surgical robot which control and drive movement of the articulated portion and the end effector. The shaft may thereby facilitate positioning of the articulated portion and end effector in the required area relative to a patient. The articulated portion may comprise a plurality of joints positioned adjacent to one another to provide degrees of freedom of movement to the end effector relative to the shaft. Lastly, the end effector may be adapted to carry out particular actions required in surgical procedures.

In known surgical instruments the joints of the articulated portion are controlled independently. This means articulated portions with a high number of joints to provide greater range of movement are complex and expensive due to the number of components required to drive movement of each joint. Alternatively, to keep complexity and cost down, the number of joints is reduced and the range of movement achievable is limited.

SUMMARY OF THE INVENTION

According to a first aspect of the invention there is provided an articulated member for a surgical instrument, the articulated member comprising a proximal end, a distal end and a plurality of rotatable joints positioned in series between the proximal end and the distal end, the plurality of rotatable joints comprising:

a first proximal joint and a first distal joint, each of which is rotatable about a respective axis that extends across a first rotation plane extending longitudinally through the articulated member;

a second proximal joint and a second distal joint, each of which is rotatable about a respective axis that extends across a second rotation plane extending longitudinally through the articulated member perpendicularly to the first rotation plane so that the second proximal and distal joints are rotatable orthogonally relative to the first proximal and distal joints;

a plurality of coupling tendon receiving portions extending longitudinally through the articulated member spaced apart from both the first and second rotation planes;

a junction positioned between the proximal and distal joints, the junction allowing passage of a coupling tendon from one coupling tendon receiving portion to a different coupling tendon receiving portion; and a plurality of coupling tendons extending through the articulated member via respective coupling tendon receiving portions, wherein each coupling tendon is fixed between the proximal end and the distal end and extends along the articulated member substantially spaced apart from both the first and second rotation planes so that rotation of one of the first proximal and distal joints causes rotation of the other of the first proximal and distal joints, and rotation of one of the second proximal and distal joints causes rotation of the other of the second proximal and distal joints.

To understand why rotation of one of the first proximal and distal joints causes rotation of the other of the first proximal and distal joints (and why rotation of one of the second proximal and distal joints similarly causes rotation of the other of the second proximal and distal joints) consider the articulated member when the first proximal joint has been rotated in a first sense. The plurality of coupling tendons extends across the first proximal joint via respective coupling tendon receiving portions which are spaced apart from the first rotation plane. Therefore, rotation of the first proximal joint in the first sense causes lengths of the plurality of coupling tendons required to extend across the first proximal joint to vary.

Due to the plurality of coupling tendons being fixed between the proximal and distal ends, the change in length of each coupling tendon that is required to extend across the first proximal joint must be counteracted by a corresponding change of length of the coupling tendon required to extend across the first distal joint. Hence, the first distal joint is caused to actuate simultaneously to the first proximal joint. The same relationship is true for the second proximal and distal joints.

Accordingly, by means of the invention, two rotatable joints of an articulated member may be actuated simultaneously by causing rotation of a single one of those rotatable joints due to the at least two rotatable joints being coupled together by the plurality of coupling tendons. Therefore, the number of components required to drive actuation of an articulated member of a surgical instrument may be reduced.

Further, the junction allows articulated member to be configured so that coupled rotatable joints either rotate in the same sense as one another or in opposite senses.

For example, in a first configuration, each coupling tendon of the plurality of coupling tendons could extend through a single respective coupling tendon receiving portion such that it does not cross through either of the first and second rotation planes. This means that if, for example, the first proximal joint is rotated in a first sense then the first distal joint would rotate in a second sense opposite to the first sense due to the variation in the lengths of the plurality of coupling tendons which extend across the first proximal joint needing to be counteracted.

However, in a second configuration, each coupling tendon may cross through both of the first and second rotation planes as it extends between the proximal joints and the distal joints. This would be achieved by each coupling tendon passing from one coupling tendon receiving portion to a different coupling tendon receiving portion via the junction. The result would be that if, for example, the first proximal joint is rotated in a first sense then the first distal joint would also rotate in the first sense due to the variation in the lengths of the plurality of coupling tendons which extend across the first proximal joint needing to be counteracted.

In embodiments of the invention, the plurality of coupling tendon receiving portions may comprise at least four coupling tendon receiving portions and the plurality of coupling tendons may comprise four coupling tendons. Further, the plurality of coupling tendon receiving portions may each extend along a plane that extends longitudinally through the articulated member and equally offset from each of the first and second rotation planes.

In such embodiments of the invention, the plurality of coupling tendon receiving portions may extend through the articulated member such that two coupling tendons are positioned either side of the both the first rotation plane and the second rotation plane. This means that movements of the first proximal and distal joints can occur independently of the second proximal and distal joints, and vice versa.

In some embodiments of the invention, the coupling tendon receiving portions are evenly spaced apart from one another throughout the articulated member. This means that proximal and distal joints coupled to one another may rotate at the same rate, as well as rotating simultaneously either in the same sense or in opposite senses.

In other embodiments of the invention, the spacing between the coupling tendon receiving portions may vary along the articulated member. By varying the distance of the coupling tendons from the central axis of the articulated member, and hence from one another, the ratio of rotation between proximal and distal joints coupled to one another may also be varied. For example, if the coupling tendons extend through coupling tendon receiving portions that are closer to the centre of the articulated member in the distal portion compared to the proximal portion, an actuation of a proximal joint by a certain angle results in a larger rotation angle at the distal joint coupled to it.

In embodiments of the invention the articulated member may be split into four parts by the first and second rotation planes and each part may comprise a coupling tendon receiving portion extending therethrough. Further, each coupling tendon may comprise a proximal portion and a distal portion and each proximal portion passes through a respective part and the associated distal portion passes through an opposite part by virtue of the coupling tendon travelling from one part to the opposite part via the junction.

In such embodiments of the invention, the first proximal joint will rotate in the same sense the first distal joint and second proximal joint will rotate in the same sense as the second distal joint. The overall bending angle achievable by the articulated member may therefore be multiplied without increasing the bending angle of a particular joint.

If a large bending angle is to be achieved with a single joint, the overall articulated member will be prone to jerky and/or imprecise movements, particularly when large bending angles are required, as the action of the joint will be analogous to that of an elbow. However, if a large bending angle is to be achieved with a plurality of joints, the rotation of each joint and the movement of the overall articulated member may be much smoother and more precise. The actions of such joints would be more analogous to finger joints that work in harmony to provide greater dexterity.

Hence, by increasing the overall bending angle achievable by the articulated member without increasing the bending angle of a particular joint, the invention allows for smoother and more precise actuations of the articulated member.

In alternative embodiments of the invention, each proximal portion passes through a respective part and the associated distal portion passes through the same part by virtue of the coupling tendon bypassing the junction.

In such embodiments of the invention, the first proximal joint will rotate in an opposite sense to the first distal joint and second proximal joint will rotate in an opposite sense to the second distal joint. By simultaneously rotating two joints in opposite senses it is possible to move the distal end of the articulated member relative to the proximal end while ensuring its orientation remains constant throughout the movement. This may be particularly useful in applications where an instrument part, such as an end effector or a proximal end of another articulated member, coupled to the distal end needs to be maintained in a constant orientation while moving between different locations. One such application may be when two or more surgical instruments are used for a surgical procedure with single-port access. In order that two surgical instruments can operate on the same region without clashing with one another, it is useful to separate the surgical instruments from one another while maintaining a constant orientation. This may be done by incorporating an articulated member according to such embodiments of the invention into each surgical instrument.

In embodiments of the invention, the articulated member may further comprise a plurality of modules rotatably engageable with one another and positioned in series whereby at least one of the rotatable joints is formed by two adjacent modules.

In such embodiments of the invention, the modules may be interchangeable and/or it may be possible to add or remove modules to increase or reduce the number of rotatable joints forming part of the articulated member. A faulty or damaged module could also be replaced, if necessary.

In embodiments of the invention, each module may comprise a junction and plurality of coupling tendon receiving sections, each coupling tendon receiving section forming part of a respective coupling tendon receiving portion.

In other words, the articulated member may comprise a plurality of junctions and coupling tendons could pass through no junctions, one junction or a plurality of junctions depending on how many rotatable joints are included in the articulated member and the types(s) of actuations required of the articulated member for a particular actuation.

Also, each coupling tendon receiving portion may be formed, at least in part, by the combination of a plurality of coupling tendon receiving sections in a respective plurality of modules. Accordingly, each coupling tendon receiving portion is able to extend the from the proximal end to the distal end irrespective of how many modules are included in the articulated module.

In embodiments of the invention, each module may comprise a pair of sub-modules rigidly couplable together in at least two configurations, the at least two configurations comprising a parallel configuration and an orthogonal configuration. When the sub-modules are in the parallel configuration, two rotatable joints formed with two immediately adjacent modules may be rotatable about respective axes extending across the same rotation plane. However, when the sub-modules are in the orthogonal configuration, two rotatable joints formed with immediately adjacent modules may be rotatable about respective axes extending across separate, orthogonal, rotation planes.

The articulated member may therefore be configured with each of the plurality of joints orientated with respect to one another as required by the application the articulated member is to be used in. For example, the articulated member could be configured such that each joint is rotatable about an axis that is orthogonal to the axes the adjacent joints are rotatable about. This would mean that the bending actions achievable by the articulated member are evenly distributed along the length of the articulated member. Alternatively, a plurality of joints that are rotatable about parallel axes of rotation may be grouped together to provide more acute bending of the articulated member in that region.

In embodiments of the invention, the articulated member may further comprise an actuating tendon receiving portion extending at least partially through the articulated member and configured to receive an actuating tendon for causing rotation of at least one of the rotatable joints.

In such embodiments of the invention, an actuating tendon may extend at least partially through the articulated member and be fixed to a particular point of the articulated member depending on the rotatable joint or joints which the actuating tendon is required to rotate. For example, in embodiments of the invention where an actuating tendon is operable to cause rotation of the first proximal joint (and, by extension, the first distal joint) the actuating tendon may extend from the proximal end, through the articulated member via a respective actuating tendon receiving portion until the actuating tendon extends across the first proximal joint and then be fixed to the articulated member. In other words, a first end of the actuating tendon may be fixed to the articulated member distally with respect to the rotatable joint that the actuating tendon is intended to rotate. The actuating tendon may then, in use, be pulled (that is, a second end of the actuating tendon extending from the proximal end of the articulated member may be pulled) in order to rotate the first proximal joint.

In some embodiments of the invention, the articulated member may comprise a pair of actuating tendon receiving portions configured to receive a pair of actuating tendons that are operable antagonistically with respect to one another. That is, one of the pair of actuating tendons can be pulled to rotate a rotatable joint in one sense and the other of the pair of actuating tendons can pulled to rotate the rotatable joint in the opposite sense.

In embodiments of the invention, the distal end of the articulated member may be couplable to an end effector. Further, the articulated member may comprise an end effector tendon receiving portion configured to receive an end effector tendon for actuating the end effector, wherein the end effector tendon receiving portion extends longitudinally through the articulated member and is positioned to intersect each of the axes about which the rotatable joints are rotatable.

In such embodiments of the invention, an end effector tendon may extend through the articulated member via the end effector tendon receiving portion and be coupled to the end effector so that actuation of the end effector tendon causes actuation of the end effector. Due to the end effector tendon intersecting each axis about which respective rotatable joints may rotate, rotation of any of the various rotatable joints will have no effect (or, at most, a negligible effect) on the end effector tendon. Therefore, the end effector will not be caused to actuate unintentionally as a result of rotations taking place along the articulated member.

According to a second aspect of the invention, there is provided a surgical instrument comprising an articulated member according to the first aspect of the invention and an end effector coupled to the distal end of the articulated member.

According to a third aspect of the invention, there is provided a surgical instrument comprising: a plurality of articulated members according the first aspect of the invention, wherein the articulated members are coupled together in series and the plurality of articulated members has a proximal end and a distal end; and an end effector coupled to the distal end of the plurality of articulated members.

The surgical instrument may comprise any suitable number of articulated members according to the first aspect of the invention depending on the degree of articulation and dexterity required from the surgical instrument for a particular application.

In embodiments of the invention, at least one articulated member of the plurality of articulated members may be split into four parts by the first and second rotation planes and each part may comprise a coupling tendon receiving portion extending therethrough. Further, each coupling tendon may comprise a proximal portion and a distal portion and each proximal portion passes through a respective part and the associated distal portion passes through an opposite part by virtue of the coupling tendon travelling from one part to the opposite part via the junction.

In embodiments of the invention, a surgical instrument (according to either the second or third aspect of the invention) may further comprise a drive module for driving articulation of the or each articulated member, wherein the drive module is coupled to the proximal end of the articulated member or the plurality of articulated members.

In embodiments of the invention, a surgical instrument (according to either the second or third aspect of the invention) may further comprise an elongate shaft coupling the proximal end of the articulated member or the plurality of articulated members to the drive module.

BRIEF DESCRIPTION OF THE DRAWINGS

The invention will now be described by way of example only with reference to the accompanying drawings in which.

DETAILED DESCRIPTION OF THE EMBODIMENTS

Figure 1:
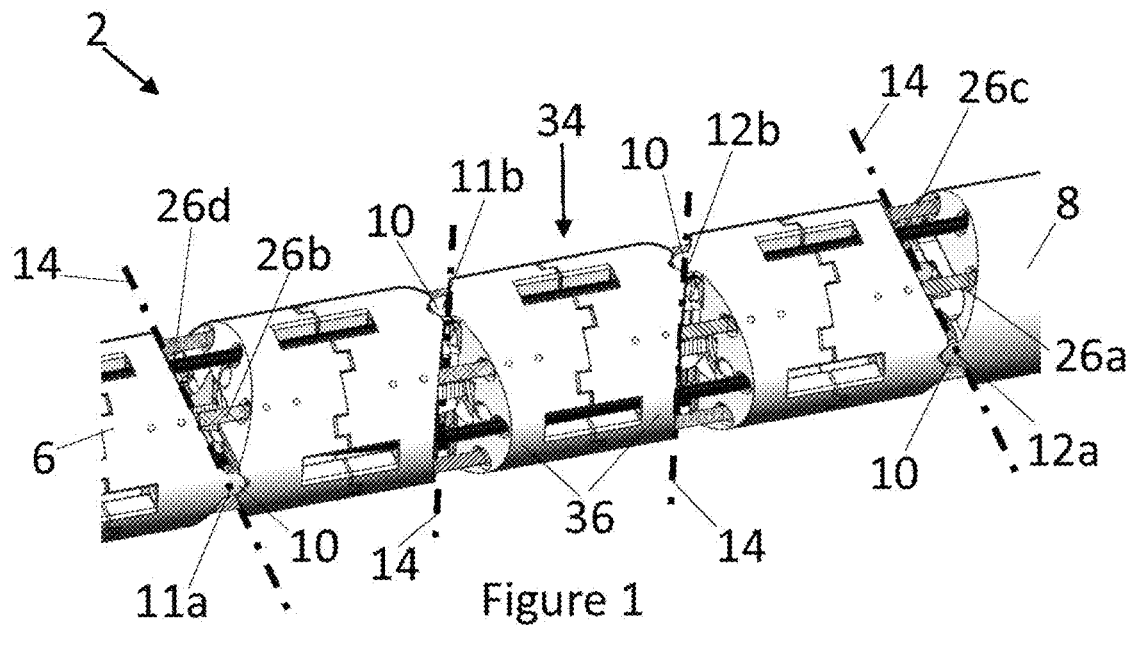
FIGS. 1 to 3 are schematic representations of an articulated member according to an embodiment of the first aspect of the invention.
Figure 2:
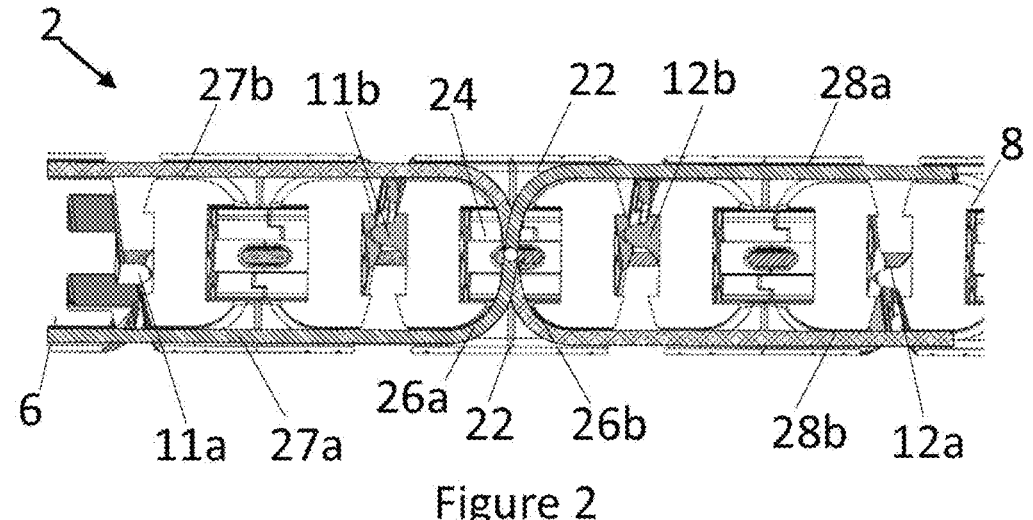
Figure 3:
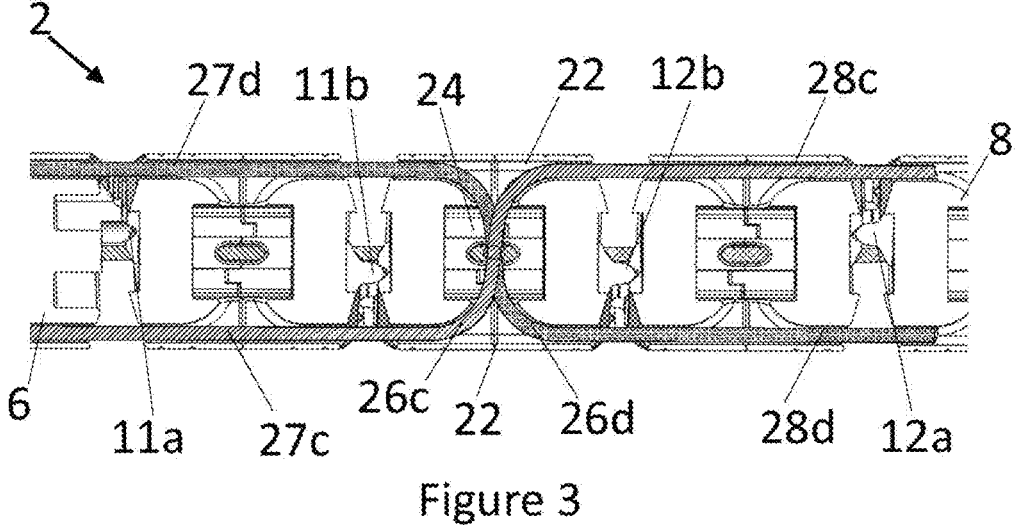

Referring initially to FIGS. 1 to 3, an articulated member according to an embodiment of the invention is designated generally by the reference numeral 2. The articulated member 2 comprises a proximal end 6, a distal end 8 and a plurality of rotatable joints 10 positioned in series between the proximal end 6 and the distal end 8.

The plurality of rotatable joints 10 comprise a first proximal joint 11a, a first distal joint 12a, a second proximal joint 11b and a second distal joint 12b. The first proximal and distal joints 11a, 12a are each rotatable about a respective axis 14 that extends across a first rotation plane extending longitudinally through the articulated member 2. Similarly, the second proximal and distal joints 11b, 12b are each rotatable about a respective axis 14 that extends across a second rotation plane extending longitudinally through the articulated member 2. The second rotation plane extends perpendicularly to the first rotation plane so that the second proximal and distal joints 11b, 12b are rotatable orthogonally relative to the first proximal and distal joints 11a, 12a.

Figure 4:
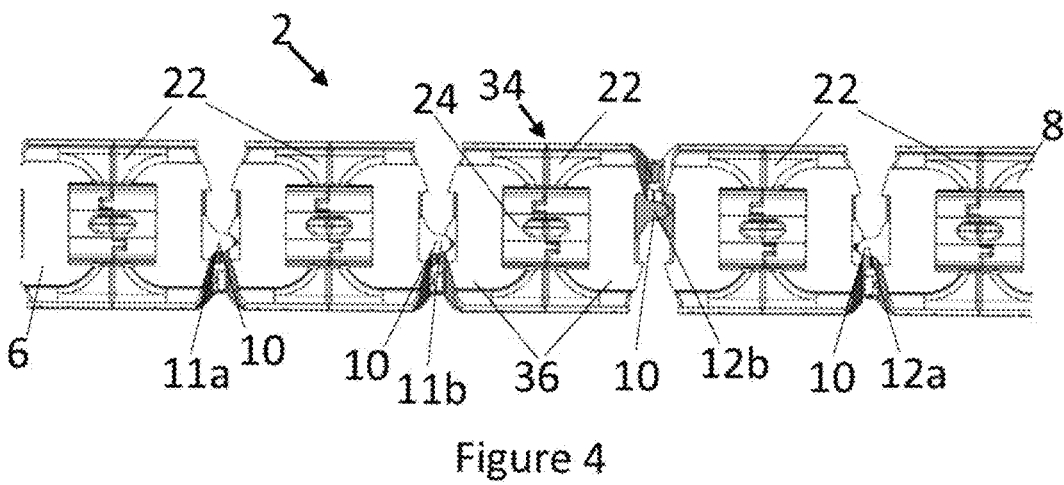
FIG. 4 is a schematic representation of the articulated member shown in FIGS. 1 to 3 with coupling tendons removed.

The articulated member 2 further comprises a plurality of coupling tendon receiving portions 22, extending longitudinally through the articulated member 2, and a plurality of coupling tendons 26 extending through the articulated member 2 via respective coupling tendon receiving portions 22. The articulated member 2 also comprises a junction 24 positioned between the proximal and distal end 6, 8, the junction allowing passage of a coupling tendon 26 from one coupling tendon receiving portion 22 to a different coupling tendon receiving portion 22. (The coupling tendon receiving portions 22 and the junction 24 are particularly visible in FIG. 4 which shows the articulated member with the coupling tendons 26 removed.)

In this embodiment of the invention, the plurality of coupling tendon receiving portions 22 comprise four coupling tendon receiving portions and the plurality of coupling tendons 26 comprises first, second, third and fourth coupling tendons 26a, 26b, 26c, 26d (respectively). Each coupling tendon 26a, 26b, 26c, 26d comprises a respective proximal portion 27a, 27b, 27c, 27d and a respective distal portion 28a, 28b, 28c, 28d.

Each coupling tendon 26 is also fixed between the proximal end 6 and the distal end 8. This means that rotation of one of the first proximal and distal joints 11a, 12a causes rotation of the other of the first proximal and distal joints 11a, 12a, and rotation of one of the second proximal and distal joints 11b, 12b causes rotation of the other of the second proximal and distal joints 11b, 12b. In other words, the first proximal and distal joints 11a, 12a are coupled together, as are the second proximal and distal joints 11b, 12b.

The articulated member 2 may be considered as being split into four parts by the first and second rotation planes. Each part comprises a respective coupling tendon receiving portion 22 extending therethrough whereby each of the coupling tendon receiving portions 22 are spaced apart from both the first and second rotation planes.

Further, in this embodiment of the invention, the coupling tendon receiving portions 22 are evenly spaced apart from one another throughout the articulated member 2. Further still, each coupling tendon receiving portion 22 extends along a plane that extends longitudinally through the articulated member and offset from the first and second rotation planes by 45 degrees.

In addition to the first and second rotation planes representing the directions through which rotatable joints 10 are rotatable, the first and second rotation planes also represent planes of symmetry. By virtue of the symmetry running through the articulated member 2, the first proximal and distal joints 11a, 12a are coupled together such that rotation of one the joints causes a rotation of the other joint by an equal magnitude. The same is true for the coupling of the second proximal and distal joints 11b, 12b.

Also, in this embodiment of the invention, each coupling tendon 26a, 26b, 26c, 26d passes from one coupling tendon receiving portion 22 to a different coupling tendon receiving portion 22 via the junction 24. In particular, each proximal portion 27a, 27b, 27c, 27d passes through a respective part while the associated distal portion 28a, 28b, 28c, 28d passes through an opposite part by virtue of the coupling tendon 26a, 26b, 26c, 26d travelling from one part to the opposite part via the junction 24.

This passage of the coupling tendons 26 thorough the junction causes the first proximal and distal joints 11a, 12a to be coupled such that they will both rotate in the same direction, and the same is true of the second proximal and distal joints 11b, 12b.

Figure 5:
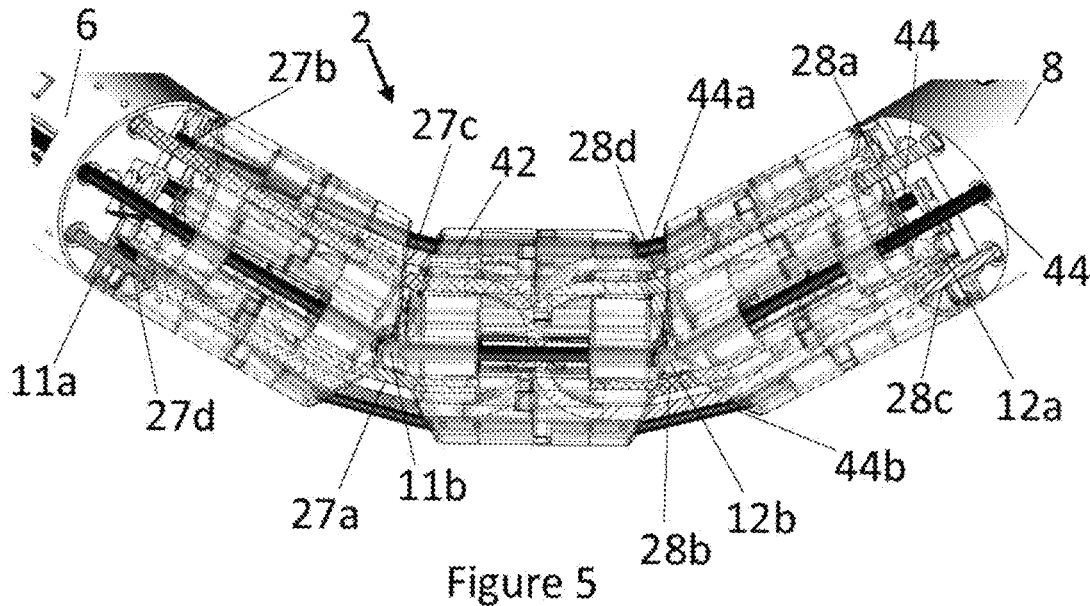
FIGS. 5 and 6 are schematic representations of the articulated member shown in FIGS. 1 to 3 when in a non-linear configuration.
Figure 6:
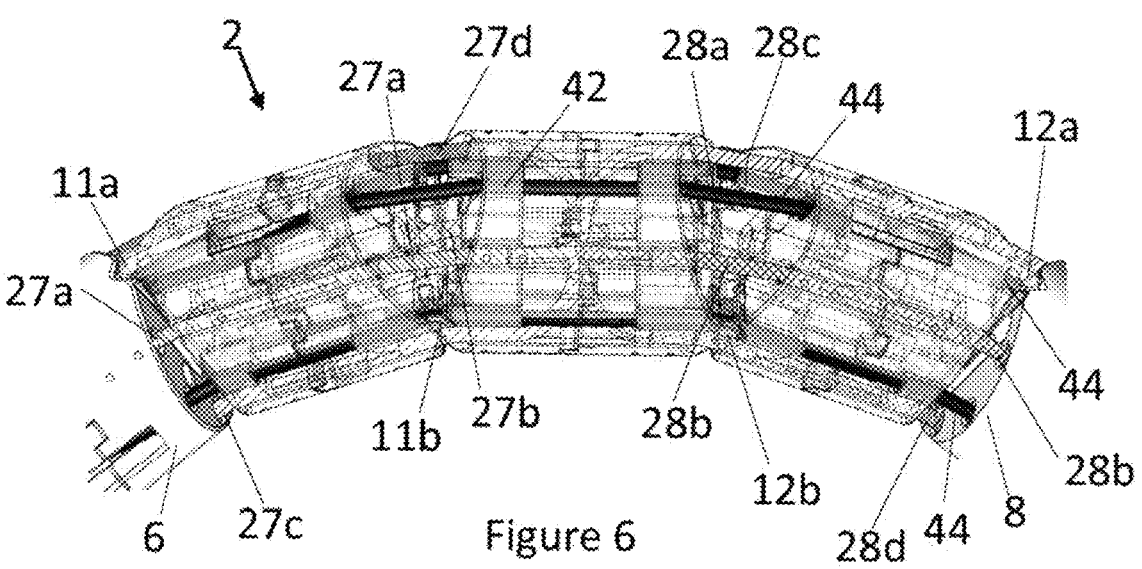

FIGS. 5 and 6 demonstrate this coupling of the first proximal and distal joints and the second proximal and distal joints.

Referring particularly to FIG. 5, it may be seen that the first proximal joint 11a has rotated away from the linear configuration shown in FIGS. 1 to 3 such that the proximal end 6 has rotated away from the reader (that is, the reader's point of view when viewing the articulated member 2 on the page). The length of each coupling tendon 26a, 26b, 26c, 26d required to extend across the first proximal joint 11a has changed as a result. In particular, more of the second and fourth proximal portions 27b and 27d are now exposed as they extend across the first proximal joint 11a.

Due to each of the coupling tendons 26a, 26b, 26c, 26d being of a fixed length between the proximal and distal ends 6, 8, the variation in the lengths of the second and fourth coupling tendons 26b, 26d required to extend across the first proximal joint 11a needs to be balanced by a corresponding variation of the first distal joint 12a. In other words, the lengths of the second and fourth distal portions 28b and 28d which extend across the first distal joint 12a must reduce (as is more clearly visible in FIG. 6), thereby causing rotation of the first distal joint 12a in the same sense as the first proximal joint 11a, i.e., away from the reader.

Meanwhile, the length of the first and third distal portions 28a, 28c required to extend across the first distal joint 11b has increased. This variation in the lengths of the first and third coupling tendons 26a, 26c required to extend across the first distal joint 12a must also be balanced. Hence, the lengths of the first and third proximal portions 27a, 27c which extend across the first proximal joint 11a must reduce (as is more clearly visible in FIG. 6). The equal and opposite actions of the first and third coupling tendons 26a, 26c relative to the second and fourth coupling tendons 26b, 26d ensures that there is no backlash in the movements of the articulated member 2.

The second proximal and distal joints 11*b*, 12*b* are coupled in much the same way as the first proximal and distal joints 11*a*, 12*a* except that the first and fourth coupling tendons 26*a*, 26*d* work against the second and third coupling tendons 26*b*, 26*c*, rather than the first and third coupling tendons 26*a*, 26*c* working against the second and fourth coupling tendons 26*b*, 26*d* as they do for the first proximal and distal joints. As is the case with the first proximal and distal joints 11*a*, 12*a*, the second proximal joint 11*b* is caused to rotate in the same sense as the second distal joint 12*b*.

The articulated member 2 further comprises a plurality of actuating tendon receiving portions 42 extending at least partially through the articulated member 2. Each actuating tendon receiving portion 42 is configured to receive an actuating tendon 44.

In this embodiment of the invention, pairs of actuating tendons 44 may be operated antagonistically with respect to one another in order to rotate a particular rotatable joint 10. For example, in FIG. 5, a pair of actuating tendons 44*a*, 44*b* extend through the articulated member 2, substantially along the second rotation plane, until they extend across the second distal joint 12*b* and are then fixed to the articulated member 2. In use, the actuating tendon 44*a* may be pulled, thereby causing the second distal joint 12*b* to rotate to the configuration shown in FIG. 5. Also, because the second proximal and distal joints 11*b*, 12*b* are coupled as described above, pulling the actuating tendon 44*a* additionally causes the second proximal joint 11*b* to rotate equivalently to the second distal joint 12*b*.

In other words, the coupling of rotatable joints 10 forming part of the articulated member 2 allows more than one rotatable joint 10 to be actuated by a single actuating tendon 44 (or pair of antagonistic actuating tendons 44). In this embodiment of the invention, the coupled rotatable joints 10 rotate in the same sense. This allows the overall bending angle which needs to be achieved to be spread over two or more joints which in turn allows the bending actuation to be carried out more smoothly than if it were to be attempted with just one rotatable joint.

Referring now to FIGS. 7 to 10, an articulated member 102 is similar to the articulated member 2 shown in FIGS. 1 to 3 except that the plurality of coupling tendons 126 extend linearly through the articulated member 102 such that each proximal portion 127*a*, 127*b*, 127*c*, 127*d* passes through the same part of the articulated member 102 as the respective distal portion 128*a*, 128*b*, 128*c*, 128*d*. This is achieved by the plurality of coupling tendons 126 simply bypassing the junction 24 as they extend through the articulated member 102.

Similarly, to the articulated member 2 shown in FIGS. 1 to 3, the plurality of rotatable joints 10 comprise a first proximal joint 111*a*, a first distal joint 112*a*, a second proximal joint 111*b* and a second distal joint 112*b*. The first proximal and distal joints 111*a*, 112*a* are each rotatable about a respective axis 14 that extends across a first rotation plane extending longitudinally through the articulated member 2. Also, the second proximal and distal joints 111*b*, 112*b* are each rotatable about a respective axis 14 that extends across a second rotation plane extending longitudinally through the articulated member 2, wherein the second rotation plane extends perpendicularly to the first rotation plane so that the second proximal and distal joints 112*a*, 112*b* are rotatable orthogonally relative to the first proximal and distal joints 111*a*, 111*b*.

As is the case for the articulated member 2 shown in FIGS. 1 to 3, the first proximal and distal joints 111*a*, 112*a* are coupled together by the plurality of coupling tendons 126, as are the second proximal and distal joints 111*b*, 112*b*.

However, as a result of the plurality of coupling tendons 126 bypassing the junction 24, when one of the rotatable joints 10 rotates, the coupled joint rotates in the opposite direction (rather than in the same direction as in the articulated member 2).

Figures 10, 11, 12:
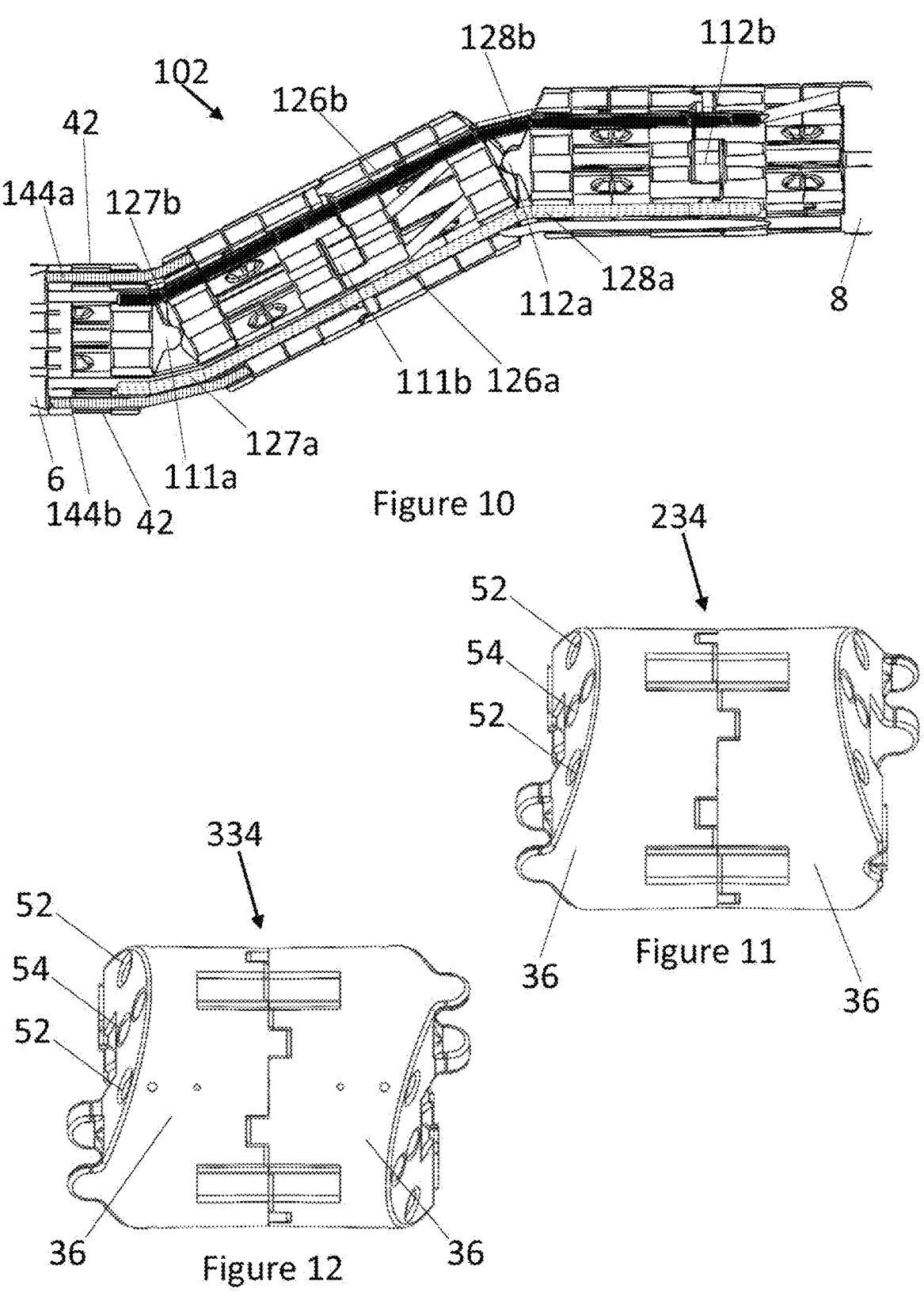
FIG. 10 is a schematic representation of the articulated member shown in FIGS. 7 to 9 when in a non-linear configuration.
FIG. 11 is a schematic representation of a module forming part of an articulated member according to the first aspect of the invention, the module comprising sub-modules in a parallel configuration.
FIG. 12 is a schematic representation of a module forming part of an articulated member according to the first aspect of the invention, the module comprising sub-modules in an orthogonal configuration.

FIG. 10 demonstrates this coupling of the first proximal and distal joints 111*a*, 112*a* in particular.

The articulated member 102 comprises a plurality of actuating tendon receiving portions 42 extending at least partially through the articulated member 102. Each actuating tendon receiving portion 42 is configured to receive an actuating tendon 144.

In this embodiment of the invention, a pair of actuating tendons 144*a*, 144*b* extend through the articulated member 102, substantially along the first rotation plane, until they extend across the first proximal joint 111*a* and are then fixed to the articulated member 102. In use, the actuating tendon 44*a* may be pulled, thereby causing the first proximal joint 111*a* to rotate to the configuration shown in FIG. 10.

This rotation of the first proximal joint 111*a* means that the lengths of the first proximal portion 127*a* and the third proximal portion 127*c* (not shown in FIG. 10 but visible in FIG. 8) required to extend across the first proximal joint 11*a* increases. Due to the plurality of coupling tendons 126 being of fixed length, the lengths of the first distal portion 128*a* and the third distal portion 128*c* that extend across the first distal joint 112*a* must reduce, thereby causing rotation of the first distal joint 112*a*.

As each of the first and third coupling tendons 126*a*, 126*c* extend along just a single part of the articulated member 102, the first proximal and distal joints 111*a*, 112*a* are caused to rotate in opposite directions. This allows the distal end 8 to be movable in such away that it remains in a similar orientation to the proximal end 6.

In fact, in this embodiment of the invention, the coupling tendon receiving portions 22 are evenly space apart throughout the articulated member 102. This means that the rotation of coupled joints will be of equal magnitude so that the distal end 8 will remain substantially in parallel alignment with the proximal end 6. However, in other embodiments of the invention, the spacing of the coupling tendon receiving portions may vary along the articulated member. This causes coupled joints to rotate at different rates to one another such that the proximal and distal ends 6, 8 may not remain in parallel alignment with one another. The variation in orientation will still be limited though as the rotation of each coupled joint will go at least some way to counteracting the rotation of the other joint.

Meanwhile, the length of the second and fourth distal portions 128*b*, 128*d* required to extend across the first distal joint 111*b* is increased by the rotations of the first proximal and distal joints 111*a*, 112*a*. This variation in the lengths of the second and fourth coupling tendons 126*b*, 126*d* required to extend across the first distal joint 112*a* must also be balanced. Hence, the lengths of the second and fourth proximal portions 127*b* and 127*d* which extend across the first proximal joint 111*a* must reduce (as is particularly visible in FIG. 10 for the second proximal portion 127*b*). The equal and opposite actions of the first and third coupling tendons 126*a*, 126*c* relative to the second and fourth coupling tendons 126*b*, 126*d* ensures that there is no backlash in the movements of the articulated member 102, similarly to the articulated member 2 shown in FIGS. 1 to 3.

The articulated members 2, 102 shown in FIGS. 1 to 10 each comprise a plurality of modules 34 rotatably engageable with one another and positioned in series whereby a plurality of the rotatable joints 10 are formed by two adjacent modules 34.

Referring now to FIG. 11, a module 234 comprises a pair of sub-modules 36 rigidly coupled together in a parallel configuration whereby the two rotatable joints that may be formed with two immediately adjacent modules (not shown) are rotatable about respective axes extending across the same rotation plane.

In contrast, in FIG. 12, a module 334 comprises a pair of sub-modules 36 rigidly coupled together in an orthogonal configuration whereby the two rotatable joints that may be formed with immediately adjacent modules (not shown) are rotatable about respective axes extending across separate, orthogonal, rotation planes.

Accordingly, it may be understood that an articulated member, such as the articulated members 2, 102 shown in FIGS. 1 to 10, may be constructed from a plurality of modules 234, a plurality of modules 334 or a combination of the two types of module 234, 334 to provide an articulated member that is rotatable about the desired combination of axes 14.

Figures 13, 14:
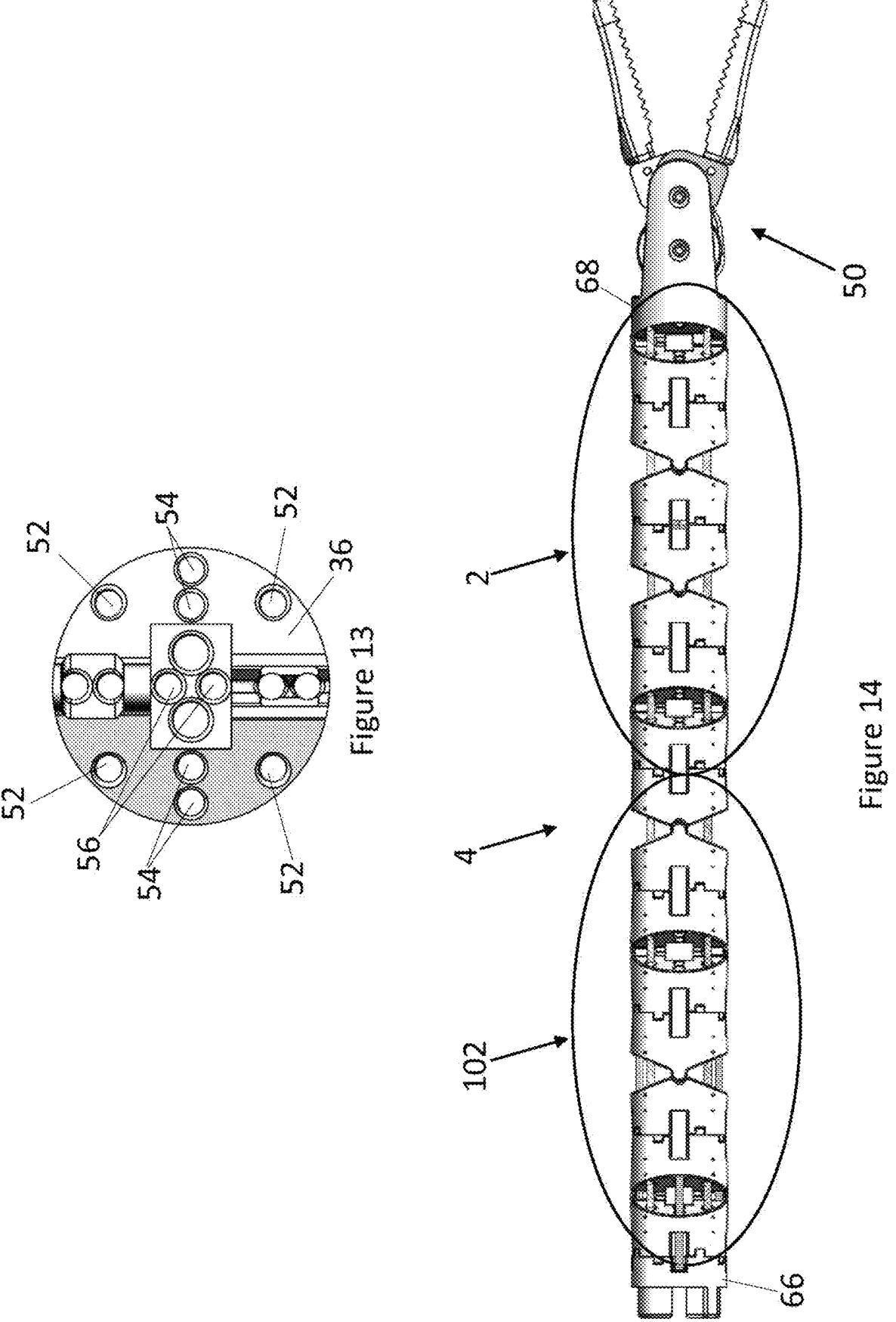
FIG. 13 is a schematic representation of a sub-module forming part of the modules shown in FIGS. 11 and 12.
FIG. 14 is a schematic representation of a surgical instrument according to an embodiment of the third aspect of the invention.

Referring now to FIG. 13, each sub-module 36 comprises a plurality of coupling tendon receiving sections 52 which are alignable with the coupling tendon receiving sections 52 of another submodule 36 when the two sub-modules 36 are coupled together, either in the parallel configuration (FIG. 11) or the orthogonal configuration (FIG. 12). The aligned coupling tendon receiving sections 52 of a plurality of modules 34 forming part of an articulated member form the coupling tendon receiving portions 22.

Each sub-module further comprises actuating tendon receiving sections 54 which similarly align with actuating tendon receiving sections 54 of other sub-modules to form the actuating tendon receiving portions 42 through which respective actuating tendons 44 may extend.

Figure 7:
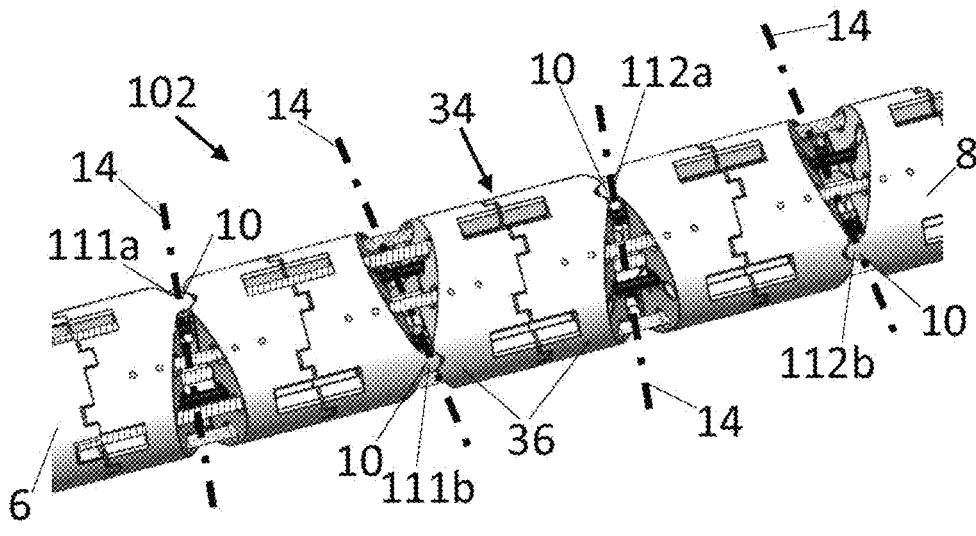
FIGS. 7 to 9 are schematic representations of an articulated member according to another embodiment of the first aspect of the invention.
Figure 8:
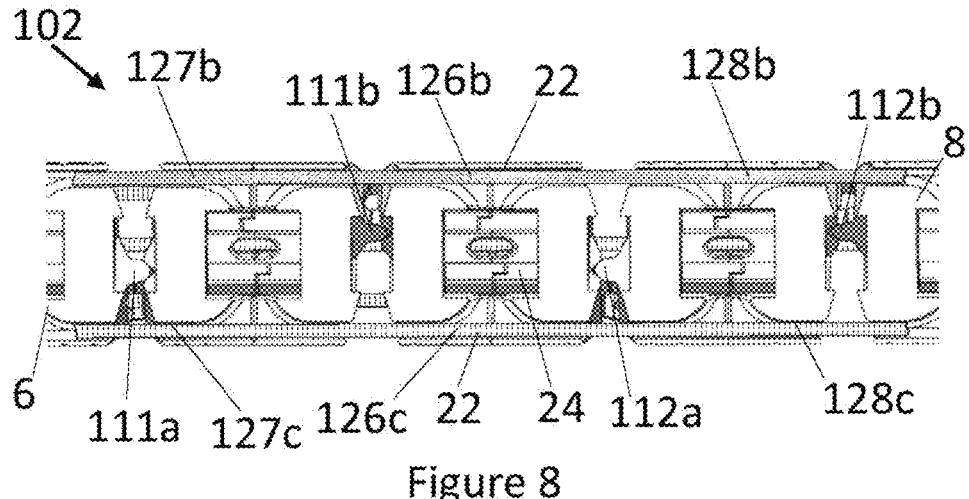
Figure 9:
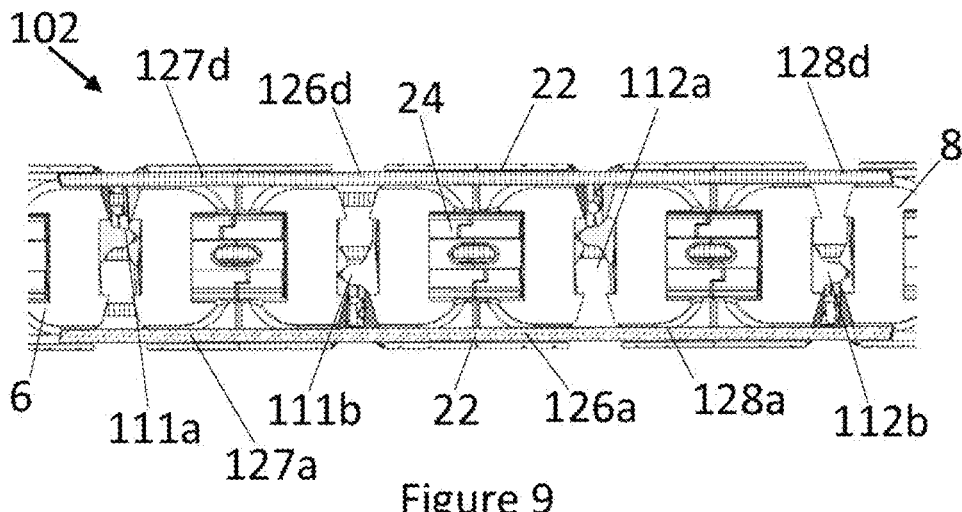

Referring now to FIG. 14, a surgical instrument 4, according to the third aspect of the invention, comprises the articulated member 2 (shown in FIGS. 1 to 3) coupled to the articulated member 102 (shown in FIGS. 7 to 9). The pair of articulated members 2, 102 have a proximal end 66 and a distal end 68. Coupled to the distal end 68 is an end effector 50 which, in this embodiment of the invention comprises a pair of rotatable jaws 62.

Figures 15, 16:
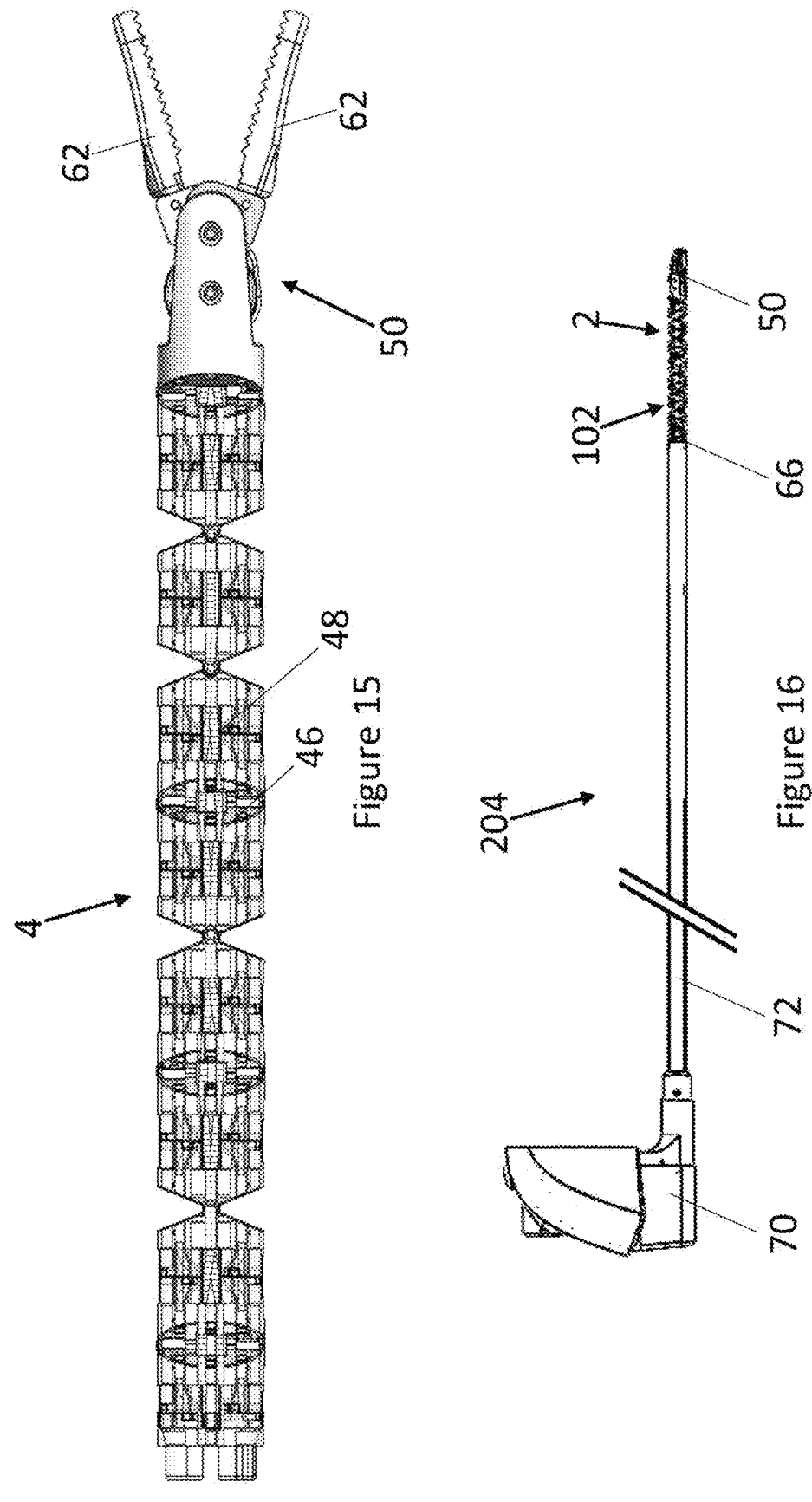
FIG. 15 is a schematic representation of the surgical instrument shown in FIG. 14, particularly showing end effectors tendons forming part of the surgical instrument.
FIG. 16 is a schematic representation of a surgical instrument according to another embodiment of the third aspect of the invention.

In FIG. 15, the surgical instrument further comprises a pair of end effector tendons 48 for actuating the end effector 50. For example, the end effector tendons 48 may be actuated to open and close jaws 62 of the end effector 50.

The articulated members 2, 102 comprise a pair of end effector tendon receiving portions 46 through which the end effector tendons 48 extend longitudinally through the articulated members 2, 102 from the proximal end 66 to the end effector 50. The end effector tendon receiving portions 46 are positioned to intersect each of the axes 14 about which the rotatable joints 10 are rotatable. In particular, in this embodiment of the invention, the end effector tendon receiving portions 46 comprise a plurality of end effector tendon receiving sections 56 (shown in FIG. 13) which form part of each sub-module 36. Each end effector tendon receiving section 56 extends through the respective sub-module so that it orthogonally intersects the axis about which that sub-module 36 may form part of a rotatable joint 10.

The fact that the end effector tendons 48 intersect each axis 14 means that rotation of the various rotatable joints 10 will have no effect (or, at most, a negligible effect) on the end effector tendons 48. Therefore, the end effector 50 will not be caused to actuate unintentionally as a result of rotations taking place along the articulated members 2, 102.

Referring now to FIG. 16, a surgical instrument 204, according to the third aspect of the invention, is similar to the surgical instrument shown in FIGS. 14 and 15 except that it additionally comprises a drive module 70 and an elongate shaft 72 coupling the proximal end 66 of the plurality of articulated members 2, 102 to the drive module 70. The drive module 70 is configured for driving articulation of the articulated members 2, 102.

The invention claimed is:

1. An articulated member for a surgical instrument, the articulated member comprising a proximal end, a distal end and a plurality of rotatable joints positioned in series between the proximal end and the distal end, the plurality of rotatable joints comprising:

a first proximal joint and a first distal joint, each of which is rotatable about a respective axis that extends across a first rotation plane extending longitudinally through the articulated member;

a second proximal joint and a second distal joint, each of which is rotatable about a respective axis that extends across a second rotation plane extending longitudinally through the articulated member perpendicularly to the first rotation plane so that the second proximal and distal joints are rotatable orthogonally relative to the first proximal and distal joints;

a plurality of coupling tendon receiving portions extending longitudinally through the articulated member spaced apart from both the first and second rotation planes;

a junction positioned between the proximal and distal joints, the junction allowing passage of a coupling tendon from one coupling tendon receiving portion to a different coupling tendon receiving portion; and a plurality of coupling tendons extending through the articulated member via respective coupling tendon receiving portions, wherein each coupling tendon is fixed between the proximal end and the distal end and extends along the articulated member substantially spaced apart from both the first and second rotation planes so that rotation of one of the first proximal and distal joints causes rotation of the other of the first proximal and distal joints, and rotation of one of the second proximal and distal joints causes rotation of the other of the second proximal and distal joints, wherein, a first coupling tendon of the plurality of coupling tendons includes a first proximal portion and a first distal portion, the first proximal portion extending from the proximal end to the junction, the first distal portion extending from the distal end to the junction, the first coupling tendon passing through the junction in between the first proximal portion and the first distal portion, the first coupling tendon passing through the first rotation plane in passing through the junction, wherein, a second coupling tendon of the plurality of coupling tendons includes a second proximal portion and a second distal portion, the second proximal portion extending from the proximal end to the junction, the second distal portion extending from the distal end to the junction, the second coupling tendon passing through the junction in between the second proximal portion and the second distal portion, the second coupling tendon passing through the first rotation plane in passing through the junction, wherein, the first proximal portion and the first distal portion are spaced from the first rotation plane, the first rotation plane being located between the first proximal portion and the first distal portion, and wherein, the first and second coupling tendons overlap at the junction as viewed along the first rotation plane.

2. An articulated member according to claim 1, wherein the plurality of coupling tendon receiving portions comprises at least four coupling tendon receiving portions and the plurality of coupling tendons comprises at least four coupling tendons.

3. An articulated member according to claim 2, wherein the plurality of coupling tendon receiving portions each extend along a plane that extends longitudinally through the articulated member and equally offset from each of the first and second rotation planes.

4. An articulated member according to claim 2, wherein the articulated member is split into four parts by the first and second rotation planes and each part comprises a coupling tendon receiving portion extending therethrough.

5. An articulated member according to claim 1, further comprising a plurality of modules rotatably engageable with one another and positioned in series whereby at least one of the rotatable joints is formed by two adjacent modules.

6. An articulated member according to claim 5, wherein each module comprises a junction and plurality of coupling tendon receiving sections, each coupling tendon receiving section forming part of a respective coupling tendon receiving portion.

7. An articulated member according to claim 5, wherein:

each module comprises a pair of sub-modules rigidly couplable together in at least two configurations, the at least two configurations comprising a parallel configuration and an orthogonal configuration;

when the sub-modules are in the parallel configuration, two rotatable joints formed with two immediately adjacent modules are rotatable about respective axes extending across the same rotation plane; and when the sub-modules are in the orthogonal configuration, two rotatable joints formed with immediately adjacent modules are rotatable about respective axes extending across separate, orthogonal, rotation planes.

8. An articulated member according to claim 1, further comprising an actuating tendon receiving portion extending at least partially through the articulated member and configured to receive an actuating tendon for causing rotation of at least one of the rotatable joints.

9. An articulated member according to claim 1, wherein the distal end of the articulated member is couplable to an end effector.

10. An articulated member according to claim 9, further comprising an end effector tendon receiving portion configured to receive an end effector tendon for actuating the end effector, wherein the end effector tendon receiving portion extends longitudinally through the articulated member and is positioned to intersect each of the axes about which the rotatable joints are rotatable.

11. A surgical instrument comprising an articulated member according to claim 1 and an end effector coupled to the distal end of the articulated member.

12. A surgical instrument comprising:

a plurality of articulated members according to claim 1, wherein the articulated members are coupled together in series and the plurality of articulated members has a proximal end and a distal end; and an end effector coupled to the distal end of the plurality of articulated members.

13. A surgical instrument according to claim 12, further comprising a drive module for driving articulation of at least one of the plurality of articulated members, wherein the drive module is coupled to the proximal end of the plurality of articulated members.

14. A surgical instrument according to claim 13, further comprising an elongate shaft coupling the proximal end of the plurality of articulated members to the drive module.

* * * * *